US008897872B2

(12) United States Patent  (10) Patent No.: US 8,897,872 B2
Sullivan  (45) Date of Patent: Nov. 25, 2014

(54) ECG ANALYSIS THAT RELATIVELY DISCOUNTS ECG DATA OF CPR PERIOD TRANSITIONS

(75) Inventor: Joseph L. Sullivan, Kirkland, WA (US)

(73) Assignee: Physio-Control, Inc., Redmond, WA (US)

( * ) Notice: Subject to any disclaimer, the term of this patent is extended or adjusted under 35 U.S.C. 154(b) by 161 days.

(21) Appl. No.: 13/012,194

(22) Filed: Jan. 24, 2011

(65) Prior Publication Data

US 2011/0118800 A1  May 19, 2011

Related U.S. Application Data

(63) Continuation-in-part of application No. 12/910,677, filed on Oct. 22, 2010, which is a continuation-in-part of application No. 12/572,691, filed on Oct. 2, 2009.

(60) Provisional application No. 61/349,441, filed on May 28, 2010.

(51) Int. Cl.
  *A61N 1/00* (2006.01)
  *A61N 1/39* (2006.01)
  *A61B 5/0452* (2006.01)

(52) U.S. Cl.
  CPC ............ *A61B 5/0452* (2013.01); *A61N 1/3925* (2013.01)
  USPC ............................................................ 607/5

(58) Field of Classification Search
  CPC ..... A61N 1/3925; A61N 1/39; A61N 1/3906; A61N 1/3912; A61N 1/3956; A61B 5/0452; A61B 7/045
  USPC .......................................................... 607/3–8
  See application file for complete search history.

(56) References Cited

U.S. PATENT DOCUMENTS

| | | | | |
|---|---|---|---|---|
| 4,296,755 | A * | 10/1981 | Judell | 600/518 |
| 7,593,772 | B2 * | 9/2009 | Sherman | 607/5 |
| 2004/0162585 | A1 * | 8/2004 | Elghazzawi et al. | 607/5 |
| 2004/0267325 | A1 * | 12/2004 | Geheb et al. | 607/5 |
| 2005/0137628 | A1 * | 6/2005 | Young et al. | 607/5 |
| 2007/0219588 | A1 * | 9/2007 | Freeman | 607/5 |
| 2010/0076510 | A1 | 3/2010 | Lyster | |

* cited by examiner

*Primary Examiner* — Catherine Voorhees
(74) *Attorney, Agent, or Firm* — Marger Johnson & McCollom PC

(57) ABSTRACT

Medical devices, software and methods are provided, for making a decision as to whether to administer electric shock therapy to a patient. The decision is made with respect to ECG data that is discounted at least partially, and sometimes even completely, if it occurs during a transition between chest compression group and a pause for ventilation.

24 Claims, 11 Drawing Sheets

*DEFIBRILLATION SCENE*

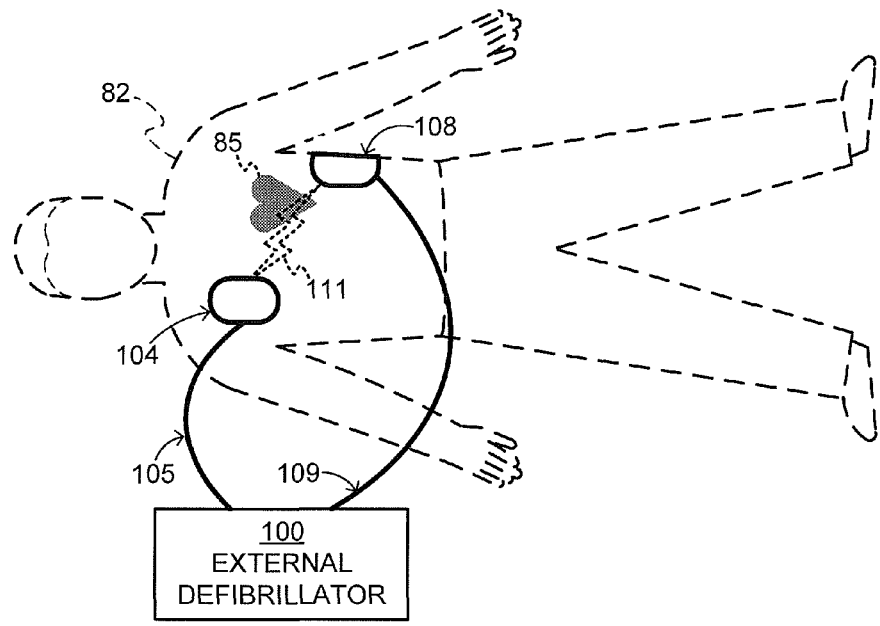
FIG. 1  *DEFIBRILLATION SCENE*
| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |
FIG. 2  *TWO MAIN TYPES OF EXTERNAL DEFIBRILLATORS*

COMPONENTS OF EXTERNAL DEFIBRILLATOR

SAMPLE PATIENT ECG DATA

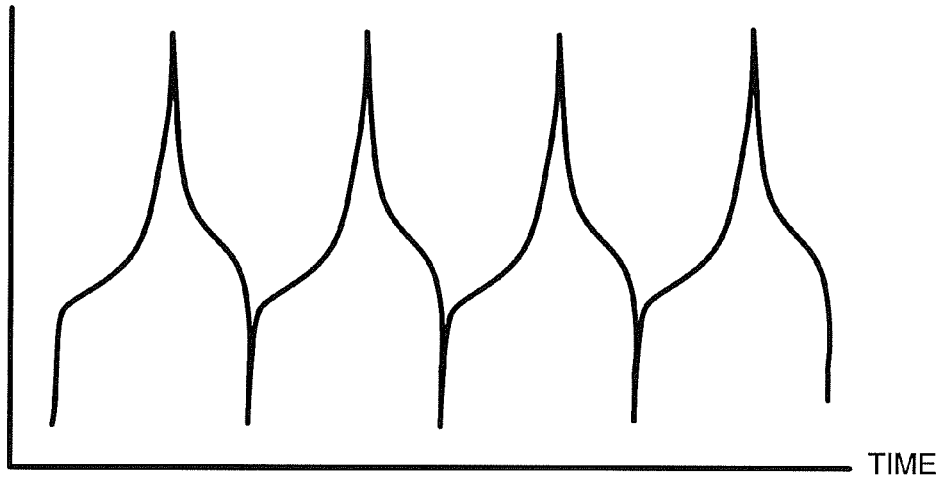
FIG. 5 *SAMPLE ECG SIGNAL HAVING IMPULSIVE ARTIFACTS AND NO QRS COMPLEXES*
FIG. 6 *SAMPLE ECG SIGNAL HAVING QRS COMPLEXES AND NO IMPULSIVE ARTIFACTS*

*METHODS*

ECG ANALYSIS THAT RELATIVELY DISCOUNTS ECG DATA OF CPR PERIOD TRANSITIONS

CROSS-REFERENCE TO RELATED APPLICATIONS

The present application claims the benefit of U.S. Provisional Patent Application Ser. No. 61/349,441, filed on May 28, 2010, the disclosure of which is hereby incorporated by reference for all purposes.

The present application is a continuation-in-part of co-pending and commonly assigned U.S. patent application Ser. No. 12/910,677, filed Oct. 22, 2010, in the name of inventor Joseph Sullivan, entitled ANALYZING ECG DATA IN DECIDING ON PATIENT CHEST COMPRESSION TREATMENT, which is a continuation-in-part of co-pending and commonly assigned U.S. patent application Ser. No. 12/572,691, filed Oct. 2, 2009, which is hereby incorporated by reference in its entirety.

FIELD

This invention generally relates to the field of defibrillators and resuscitation.

BACKGROUND

In humans, the heart beats to sustain life. In normal operation, it pumps blood through the various parts of the body. More particularly, the various chamber of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle, then, expels the blood, forcing it to circulate to the various parts of the body.

The heart chambers pump because of the heart's electrical control system. More particularly, the sinoatrial (SA) node generates an electrical impulse, which generates further electrical signals. These further signals cause the above-described contractions of the various chambers in the heart, in the right sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia, and some of it may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively, and death can occur. In fact, it is estimated that SCA results in more than 250,000 deaths per year in the United States alone. Further, a SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood. The person's condition will deteriorate rapidly and, if not reversed in time, they will die soon, e.g. within ten minutes.

Ventricular Fibrillation can often be reversed using a life-saving device called a defibrillator. A defibrillator, if applied properly, can administer an electrical shock to the heart. The shock may terminate the VF, thus giving the heart the opportunity to resume pumping blood. If VF is not terminated, the shock may be repeated, often at escalating energies.

A challenge with defibrillation is that the electrical shock must be administered very soon after the onset of VF. There is not much time: the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. First, for some people who are considered to be at a higher risk of VF, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at risk. As such, VF can be experienced by many people who lack the benefit of ICD therapy. When VF occurs to a person who does not have an ICD, they collapse, because blood flow has stopped. They should receive therapy quickly.

For a VF victim without an ICD, a different type of defibrillator can be used, which is called an external defibrillator. External defibrillators have been made portable, so they can be brought to a potential VF victim quickly enough to revive them.

During VF, the person's condition deteriorates, because the blood is not flowing to the brain, heart, lungs, and other organs. Blood flow must be restored, if resuscitation attempts are to be successful.

Cardiopulmonary Resuscitation (CPR) is one method of forcing blood flow in a person experiencing cardiac arrest. In addition, CPR is the primary recommended treatment for some patients with some kinds of non-VF cardiac arrest, such as asystole and pulseless electrical activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows the deterioration that would otherwise occur while a defibrillator is being retrieved. Indeed, for patients with an extended down-time, survival rates are higher if CPR is administered prior to defibrillation.

It is desired to improve patient outcomes, by making improved decisions of when to administer therapy, such as electrical shocks, CPR, pharmaceuticals, etc. Patient outcomes are sometimes analyzed in post-event review.

BRIEF SUMMARY

The present description gives instances of medical devices, software and methods, the use of which may help overcome problems and limitations of the prior art.

In some embodiments, a decision as to whether to administer electric shock therapy to a patient is made with respect to ECG data that is discounted at least partially, and sometimes even completely, if it occurs during a transition between chest compression group and a pause for ventilation.

An advantage over the prior art is that patient outcomes can be improved.

These and other features and advantages of this description will become more readily apparent from the following Detailed Description, which proceeds with reference to the drawings, in which:

BRIEF DESCRIPTION OF THE DRAWINGS

FIG. 1 is a diagram of a scene where an external defibrillator is used to save the life of a person according to embodiments.

FIG. 2 is a table listing two main types of the external defibrillator shown in FIG. 1, and who they might be used by.

FIG. 5 is a time diagram of an ECG signal having impulsive artifacts and no QRS complexes.

FIG. 6 is a time diagram of an ECG signal having QRS complexes and no impulsive artifacts.

DETAILED DESCRIPTION

Figure 3:
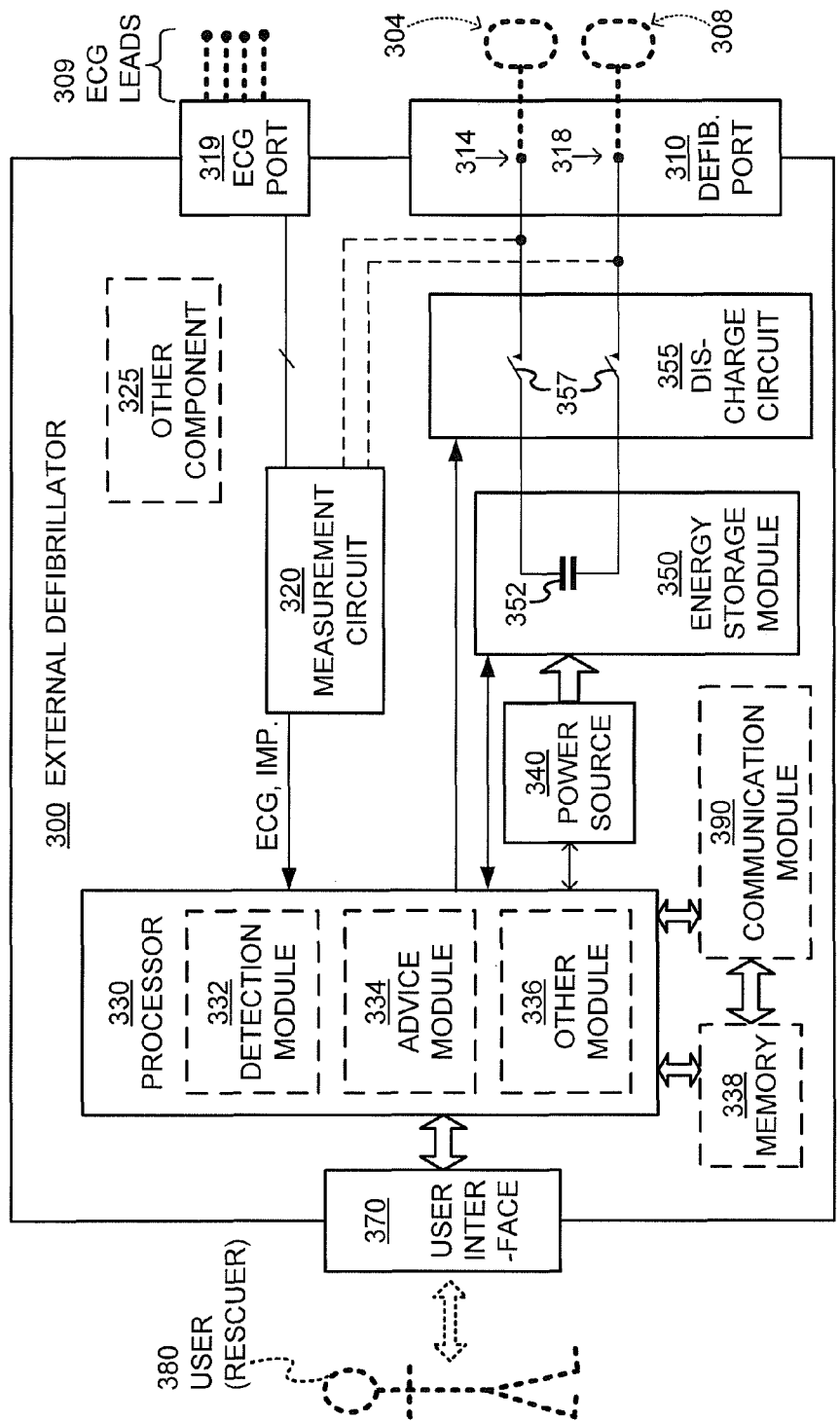
FIG. 3 is a diagram showing components of an external defibrillator, such as the one shown in FIG. 1, which is made according to embodiments.

As has been mentioned, the present description is about making a decision of whether electric therapy should be administered or not. Embodiments include medical devices that can administer electrical therapy, such as defibrillators, pacers, etc. Examples are now described.

FIG. 1 is a diagram of a defibrillation scene. A person 82 is lying on their back. Person 82 could be a patient in a hospital, or someone found unconscious, and then turned to be on their back. Person 82 is experiencing a condition in their heart 85, which could be Ventricular Fibrillation (VF).

A portable external defibrillator 100 has been brought close to person 82. At least two defibrillation electrodes 104, 108 are usually provided with external defibrillator 100, and are sometimes called electrodes 104, 108. Electrodes 104, 108 are coupled with external defibrillator 100 via respective electrode leads 105, 109. A rescuer (not shown) has attached electrodes 104, 108 to the skin of person 82. Defibrillator 100 is administering, via electrodes 104, 108, a brief, strong electric pulse 111 through the body of person 82. Pulse 111, also known as a defibrillation shock, goes also through heart 85, in an attempt to restart it, for saving the life of person 82.

Defibrillator 100 can be one of different types, each with different sets of features and capabilities. The set of capabilities of defibrillator 100 is determined by planning who would use it, and what training they would be likely to have. Examples are now described.

FIG. 2 is a table listing two main types of external defibrillators, and who they are primarily intended to be used by. A first type of defibrillator 100 is generally called a defibrillator-monitor, because it is typically formed as a unit with a patient monitor. A defibrillator-monitor is intended to be used by persons in the medical professions, such as doctors, nurses, paramedics, emergency medical technicians, etc. Such a defibrillator-monitor is intended to be used in a pre-hospital or hospital scenario.

As a defibrillator, the device can be one of different varieties, or even versatile enough to be able to switch among different modes that individually correspond to the varieties. One variety is that of an automated defibrillator, which can determine whether a shock is needed and, if so, charge to a predetermined energy level and instruct the user to administer the shock. Another variety is that of a manual defibrillator, where the user determines the need and controls administering the shock.

As a patient monitor, the device has features additional to what is minimally needed for mere operation as a defibrillator. These features can be for monitoring physiological signals of a person in an emergency scenario. For example, these signals can include a person's full ECG (electrocardiogram) signals. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on.

A second type of external defibrillator 100 is generally called an AED, which stands for "Automated External Defibrillator". An AED typically makes the shock/no shock determination by itself, automatically. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a much simpler construction, an AED typically costs much less than a defibrillator-monitor. As such, it makes sense for a hospital, for example, to deploy AEDs at its various floors, in case the more expensive defibrillator-monitor is at an Intensive Care Unit, and so on.

AEDs, however, can also be used by people who are not in the medical profession. More particularly, an AED can be used by many professional first responders, such as policemen, firemen, etc. Even a person with only first-aid training can use one. And AEDs increasingly can supply instructions to whoever is using them.

AEDs are thus particularly useful, because it is so critical to respond quickly, when a person suffers from VF. Indeed, the people who will first reach the VF sufferer may not be in the medical professions.

Increasing awareness has resulted in AEDs being deployed in public or semi-public spaces, so that even a member of the public can use one, if they have obtained first aid and CPR/AED training on their own initiative. This way, defibrillation can be administered soon enough after the onset of VF, to hopefully be effective in rescuing the person.

There are additional types of external defibrillators, which are not listed in FIG. 2. For example, a hybrid defibrillator can have aspects of an AED, and also of a defibrillator-monitor. A usual such aspect is additional ECG monitoring capability.

FIG. 3 is a diagram showing components of an external defibrillator 300 made according to embodiments. These components can be, for example, in external defibrillator 100 of FIG. 1.

External defibrillator 300 is intended for use by a user 380, who would be the rescuer. Defibrillator 300 typically includes a defibrillation port 310, such as a socket. Defibrillation port 310 includes nodes 314, 318. Defibrillation electrodes 304, 308, which can be similar to electrodes 104, 108, can be plugged in defibrillation port 310, so as to make electrical contact with nodes 314, 318, respectively. It is also possible that electrodes can be connected continuously to defibrillation port 310, etc. Either way, defibrillation port 310 can be used for guiding via electrodes to person 82 an electrical charge that has been stored in defibrillator 300, as will be seen later in this document.

If defibrillator 300 is actually a defibrillator-monitor, as was described with reference to FIG. 2, then it will typically also have an ECG port 319, for plugging in ECG leads 309. ECG leads 309 can sense a full ECG signal. Moreover, a defibrillator-monitor could have additional ports (not shown), and an other component 325 for the above described additional features.

Defibrillator 300 also includes a measurement circuit 320. Measurement circuit 320 receives physiological signals from ECG port 319, and also from other ports, if provided. These physiological signals are sensed, and information about them is rendered by circuit 320 as data, or other signals, etc.

If defibrillator 300 is actually an AED, it may lack ECG port 319. Measurement circuit 320 can obtain physiological signals through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person.

Defibrillator 300 also includes a processor 330. Processor 330 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 can be considered to have a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at advice based on outputs of detection module 332. Advice module 334 can include a Shock Advisory Algorithm, implement decision rules, and so on. The advice can be to shock, to not shock, to administer other forms of therapy, and so on. If the advice is to shock, some external defibrillator embodiments merely report that to the user, and prompt them to do it. Other embodiments further execute the advice, by administering the shock. If the advice is to administer CPR, defibrillator 300 may further issue prompts for it, and so on.

Processor 330 can include additional modules, such as module 336, for other functions. In addition, if other component 325 is indeed provided, it may be operated in part by processor 330, etc.

Defibrillator 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. The programs can be operational for the inherent needs of processor 330, and can also include protocols and ways that decisions can be made by advice module 334. In addition, memory 338 can store prompts for user 380, etc.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include AC power override, for where AC power will be available, and so on. In some embodiments, power source 340 is controlled by processor 330.

Defibrillator 300 additionally includes an energy storage module 350. Module 350 is where some electrical energy is stored, when preparing it for sudden discharge to administer a shock. Module 350 can be charged from power source 340 to the right amount of energy, as controlled by processor 330. In typical implementations, module 350 includes one or more capacitors 352, and so on.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and so on.

Defibrillator 300 further includes a user interface 370 for user 380. User interface 370 can be made in any number of ways. For example, interface 370 may include a screen, to display what is detected and measured, provide visual feedback to the rescuer for their resuscitation attempts, and so on. Interface 370 may also include a speaker, to issue voice prompts, etc. Interface 370 may additionally include various controls, such as pushbuttons, keyboards, and so on. In addition, discharge circuit 355 can be controlled by processor 330, or directly by user 380 via user interface 370, and so on.

Defibrillator 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and so on.

An additional feature of a defibrillator can be CPR-prompting. Prompts are issued to the user, visual or by sound, so that the user can administer CPR. Examples are taught in U.S. Pat. No. 6,334,070 and U.S. Pat. No. 6,356,785.

Figure 4:
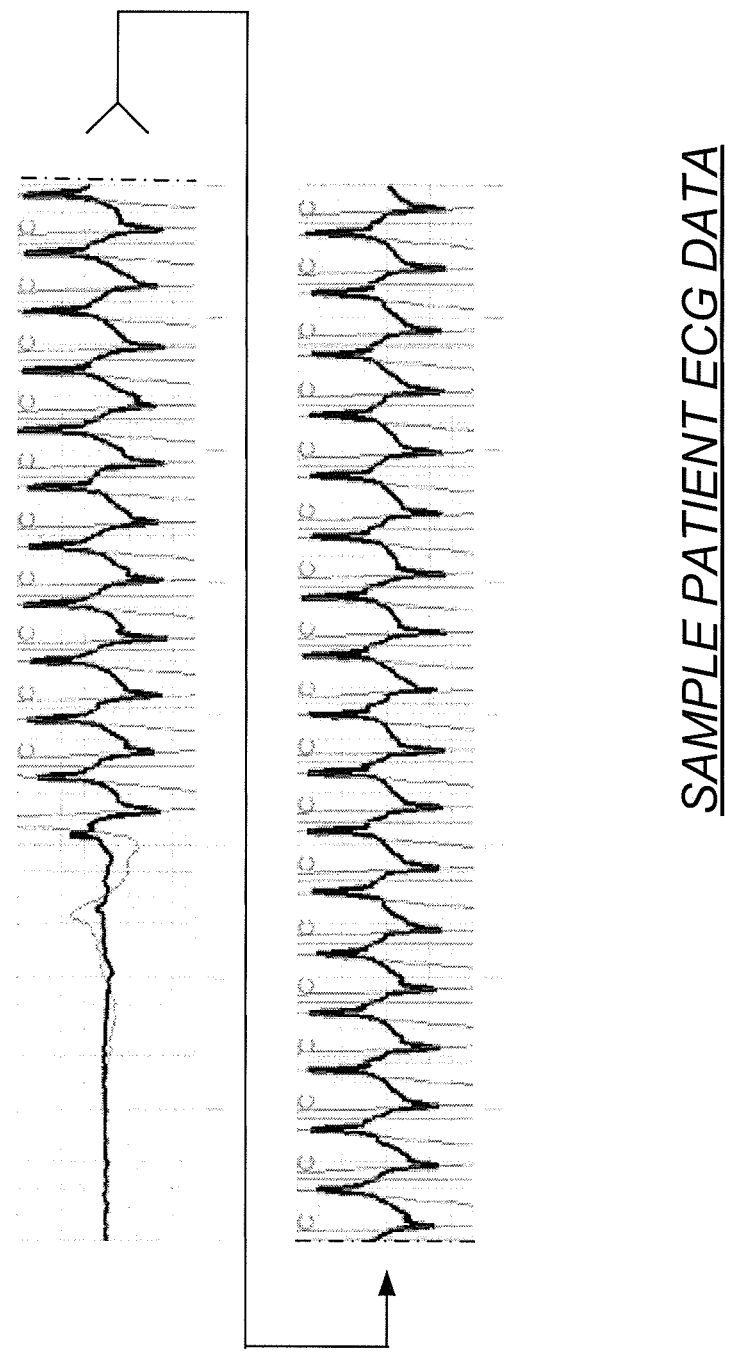
FIG. 4 is a time diagram of patient ECG data in the form of signals.

FIG. 4 is a time diagram of patient ECG data in the form of signals. The ECG data exhibits an impulsive waveform having signal spikes or peaks that include both positive peaks and negative peaks.

FIG. 5 is a time diagram of an ECG signal illustrating example signal spikes that represent impulsive signal artifacts and not QRS complexes. For example, the patient receiving chest compressions may be in a state of asystole such that the signal spikes represent only impulsive artifacts resulting from physical delivery of the chest compressions to the patient. The impulsive artifacts in the ECG signal may have both positive peaks and negative peaks.

FIG. 6 is a time diagram of an ECG signal illustrating example QRS complexes and no impulsive artifacts. The QRS complexes generally include both positive peaks and negative peaks.

As can be readily discerned by considering the two figures together, there are a number of similarities between the ECG signals of FIGS. 5 and 6. For example, the positive peaks are relatively closer in time to the corresponding negative peaks than to another positive peak. Also, the pattern of recurrence is similar. Consequently, current systems often have trouble discerning ECG signals that have impulsive artifacts and no QRS complexes from ECG signals that have QRS complexes and no impulsive artifacts.

The functions of this description may be implemented by one or more devices that include logic circuitry. The device performs functions and/or methods as are described in this document. The logic circuitry may include a processor that may be programmable for a general purpose, or dedicated, such as microcontroller, a microprocessor, a Digital Signal Processor (DSP), etc. For example, the device may be a digital computer like device, such as a general-purpose computer selectively activated or reconfigured by a computer program stored in the computer. Alternately, the device may be implemented by an Application Specific Integrated Circuit (ASIC), etc.

Moreover, methods are described below. The methods and algorithms presented herein are not necessarily inherently associated with any particular computer or other apparatus. Rather, various general-purpose machines may be used with programs in accordance with the teachings herein, or it may prove more convenient to construct more specialized apparatus to perform the required method steps. The required structure for a variety of these machines will become apparent from this description.

In all cases there should be borne in mind the distinction between methods in this description, and the method of operating a computing machine. This description relates both to methods in general, and also to steps for operating a computer and for processing electrical or other physical signals to generate other desired physical signals.

Programs are additionally included in this description, as are methods of operation of the programs. A program is generally defined as a group of steps leading to a desired result, due to their nature and their sequence. A program is usually advantageously implemented as a program for a computing machine, such as a general-purpose computer, a special purpose computer, a microprocessor, etc.

Storage media are additionally included in this description. Such media, individually or in combination with others, have stored thereon instructions of a program made according to the invention. A storage medium according to the invention is a computer-readable medium, such as a memory, and is read by the computing machine mentioned above.

Performing the steps or instructions of a program requires physical manipulations of physical quantities. Usually, though not necessarily, these quantities may be transferred, combined, compared, and otherwise manipulated or processed according to the instructions, and they may also be stored in a computer-readable medium. These quantities include, for example electrical, magnetic, and electromagnetic signals, and also states of matter that can be queried by such signals. It is convenient at times, principally for reasons of common usage, to refer to these quantities as bits, data bits, samples, values, symbols, characters, images, terms, numbers, or the like. It should be borne in mind, however, that all of these and similar terms are associated with the appropriate physical quantities, and that these terms are merely convenient labels applied to these physical quantities, individually or in groups.

This detailed description is presented largely in terms of flowcharts, display images, algorithms, and symbolic representations of operations of data bits within at least one computer readable medium, such as a memory. Indeed, such descriptions and representations are the type of convenient labels used by those skilled in programming and/or the data processing arts to effectively convey the substance of their work to others skilled in the art. A person skilled in the art of programming may use these descriptions to readily generate specific instructions for implementing a program according to the present invention.

Often, for the sake of convenience only, it is preferred to implement and describe a program as various interconnected distinct software modules or features, individually and collectively also known as software. This is not necessary, however, and there may be cases where modules are equivalently aggregated into a single program with unclear boundaries. In any event, the software modules or features of this description may be implemented by themselves, or in combination with others. Even though it is said that the program may be stored in a computer-readable medium, it should be clear to a person skilled in the art that it need not be a single memory, or even a single machine. Various portions, modules or features of it may reside in separate memories, or even separate machines. The separate machines may be connected directly, or through a network, such as a local access network (LAN), or a global network, such as the Internet.

It will be appreciated that some of these methods may include software steps which may be performed by different modules of an overall software architecture. For example, data forwarding in a router may be performed in a data plane, which consults a local routing table. Collection of performance data may also be performed in a data plane. The performance data may be processed in a control plane, which accordingly may update the local routing table, in addition to neighboring ones. A person skilled in the art will discern which step is best performed in which plane.

An economy is achieved in the present document in that a single set of flowcharts is used to describe both programs, and also methods. So, while flowcharts are described in terms of boxes, they can mean both method and programs.

For this description, the methods may be implemented by machine operations. In other words, embodiments of programs are made such that they perform methods of the invention that are described in this document. These may be optionally performed in conjunction with one or more human operators performing some, but not all of them. As per the above, the users need not be collocated with each other, but each only with a machine that houses a portion of the program. Alternately, some of these machines may operate automatically, without users and/or independently from each other.

Methods are now described.

Figure 7:
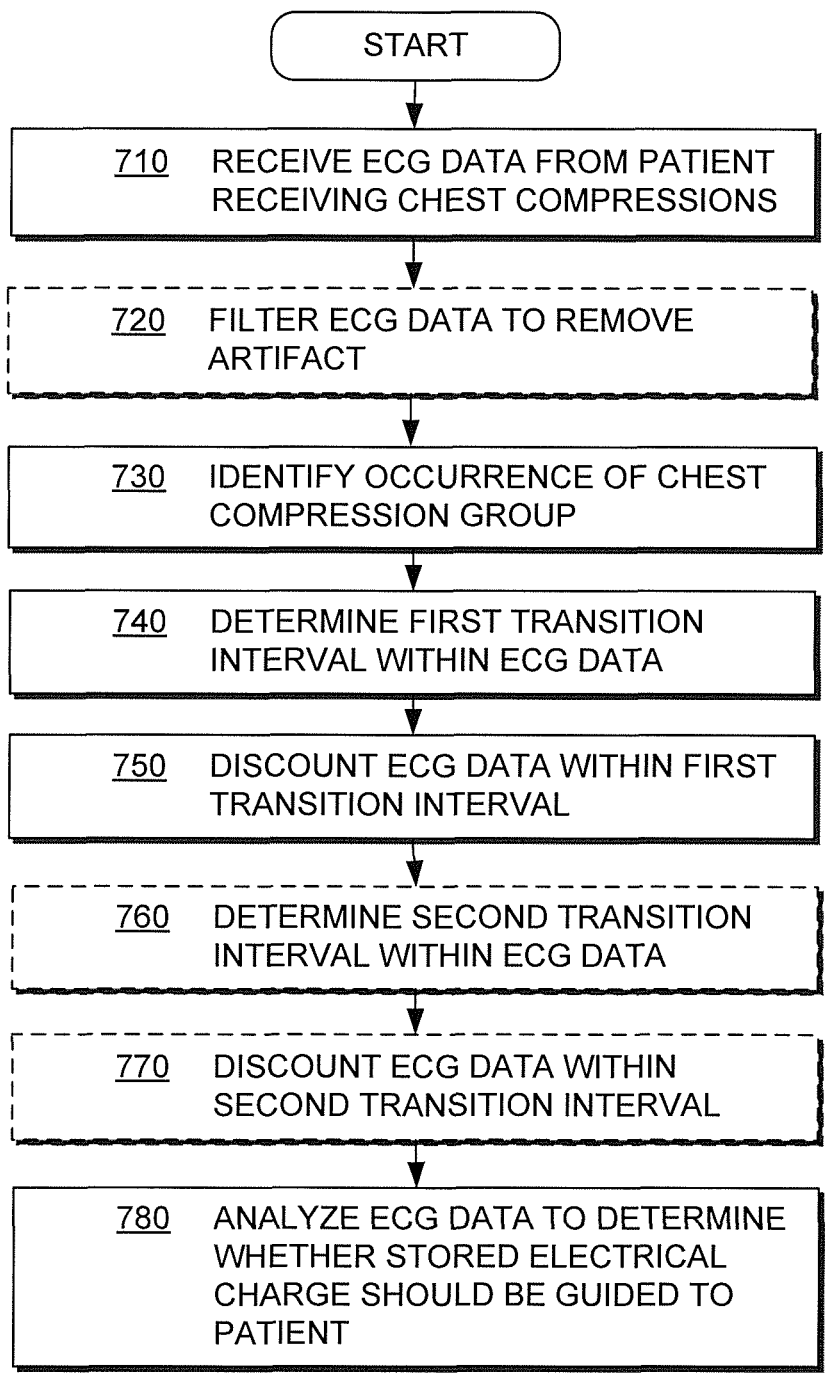
FIG. 7 is a flowchart for illustrating methods according to embodiments.

FIG. 7 shows a flowchart 700 for describing methods according to embodiments. The methods of flowchart 700 may be practiced by systems, devices, and software according to embodiments. For example, the methods illustrated by flowchart 700 can be performed by the processor 330 illustrated in FIG. 3. Or they may be performed by a processor for after-the-fact analysis, and so on.

In an operation 710 ECG data of a patient may be received. The patient at the time could be receiving chest compressions. The data could be received during cardiac resuscitation, or even after the fact during evaluation.

In an optional operation 720, the ECG data received at operation 710 may be filtered. Filtering can remove at least one artifact in the signal, which arises from chest compressions, and this is why sometimes the ECG data is referred to below as filtered data. It will be understood that the filtering operation 720 can happen at this point, or later in flowchart 700. In fact, in some embodiments, it is preferred to perform operation 720 after the transitions are identified in subsequent operations, because the type of filtering can be advantageously varied, depending on whether the segment contains compressions or not, as will become evident from the description that follows. Moreover, filtering across transitions has always been difficult, if the filtering is adaptive, as is often preferred. Indeed, adaptive filtering works best with all compressions or no compressions.

Figure 8A:
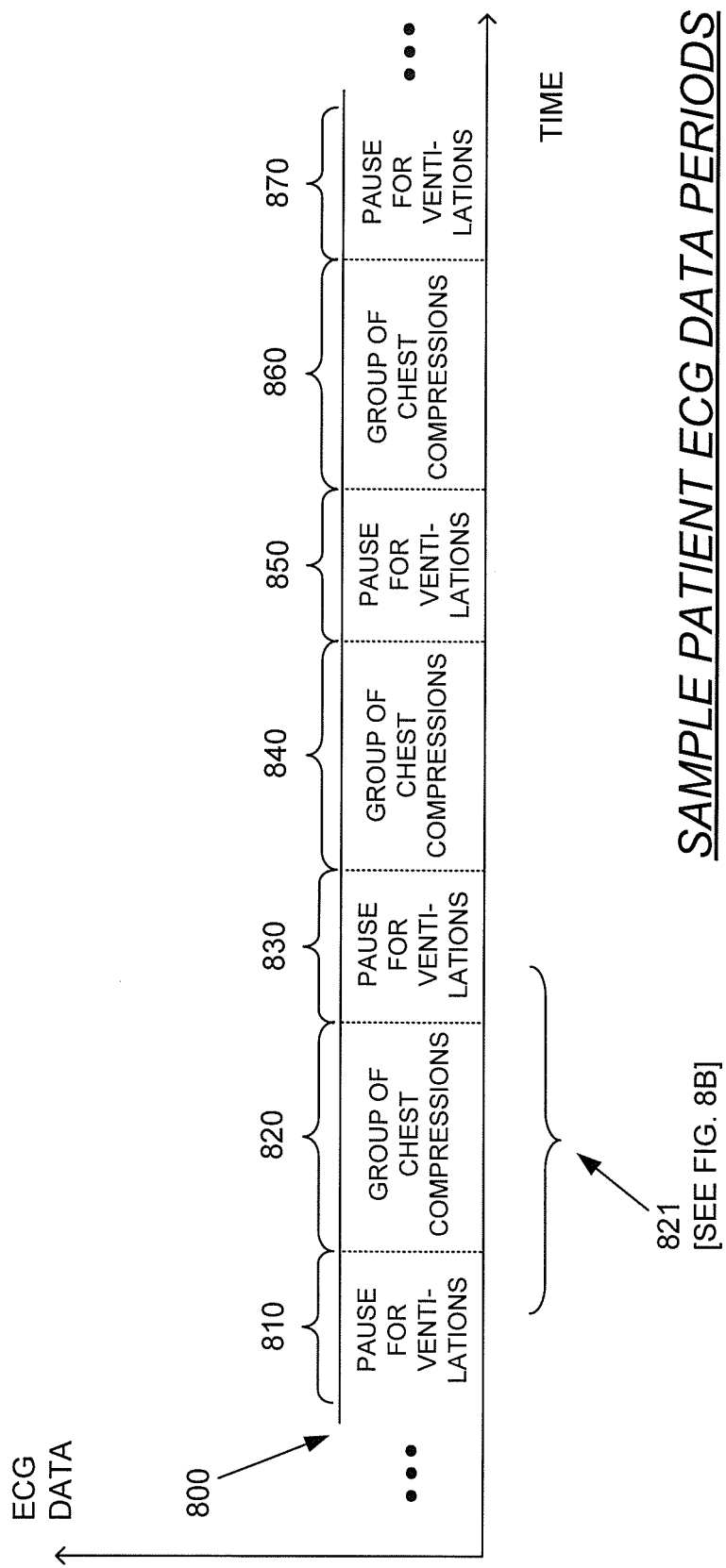
FIG. 8A is a time diagram of patient ECG data periods where chest compression groups are alternated with pauses for ventilating the patient.
Figure 8B:
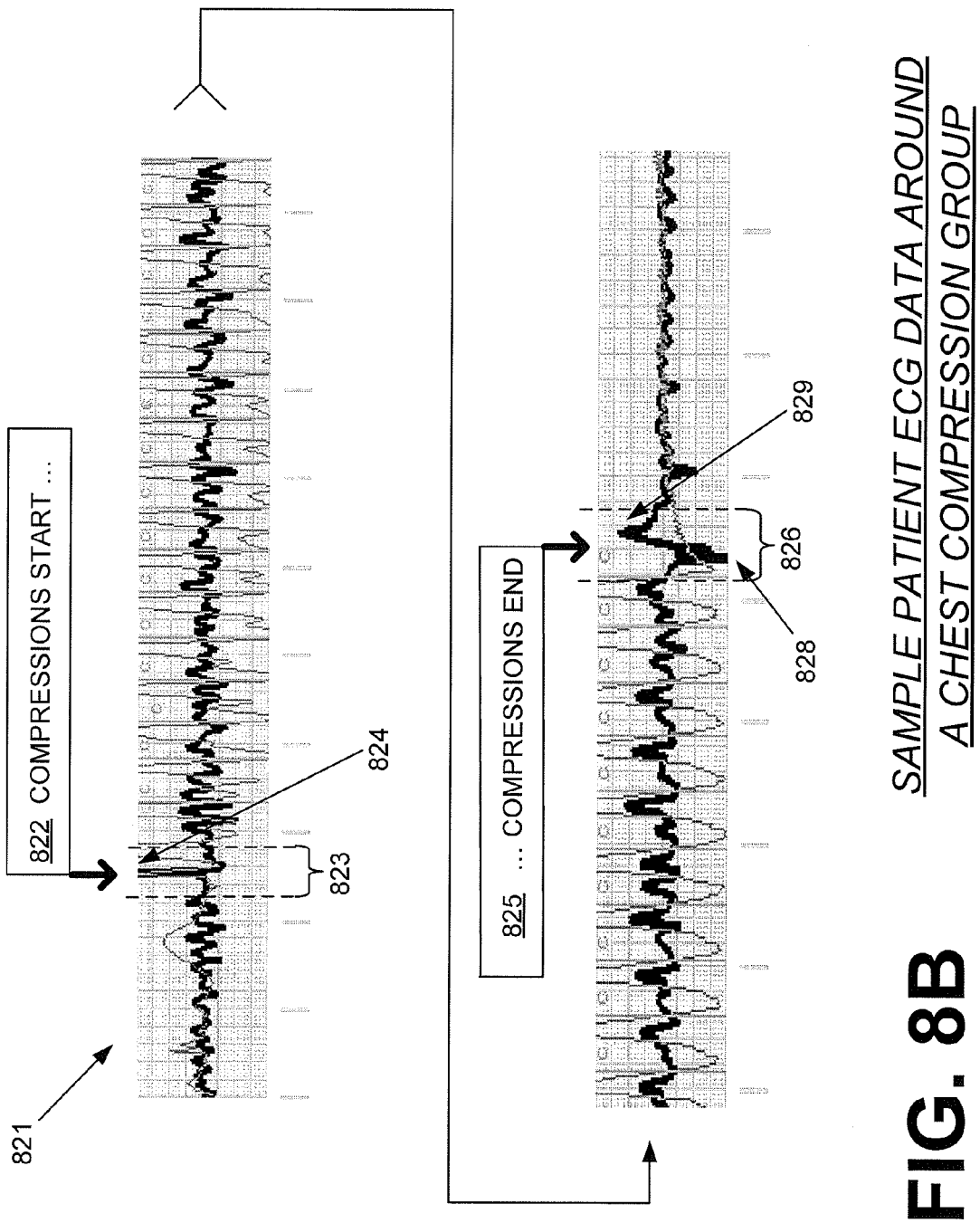
FIG. 8B is a time diagram of a segment of the patient ECG data periods of FIG. 8A, showing the CPR transition periods around a single chest compression group according to embodiments.

In an operation 730, the occurrence of at least one chest compression group may be identified within the received ECG data. As used herein, an identified chest compression group may correspond to a series of consecutive, substantially periodically repeating chest compressions being administered to the patient. FIG. 8A, discussed below, illustrates a series of chest compression groups corresponding to chest compressions that are delivered to a patient. FIG. 8B, also discussed below, illustrates a detailed example of one of the chest compression groups in FIG. 8A. To perform operation 730, chest compressions have to be identified within the data, and then groups of them can be identified. This will yield the location of chest compression groups within the data. If a compression group is not readily identified, other data segments can be searched.

Figure 8C:
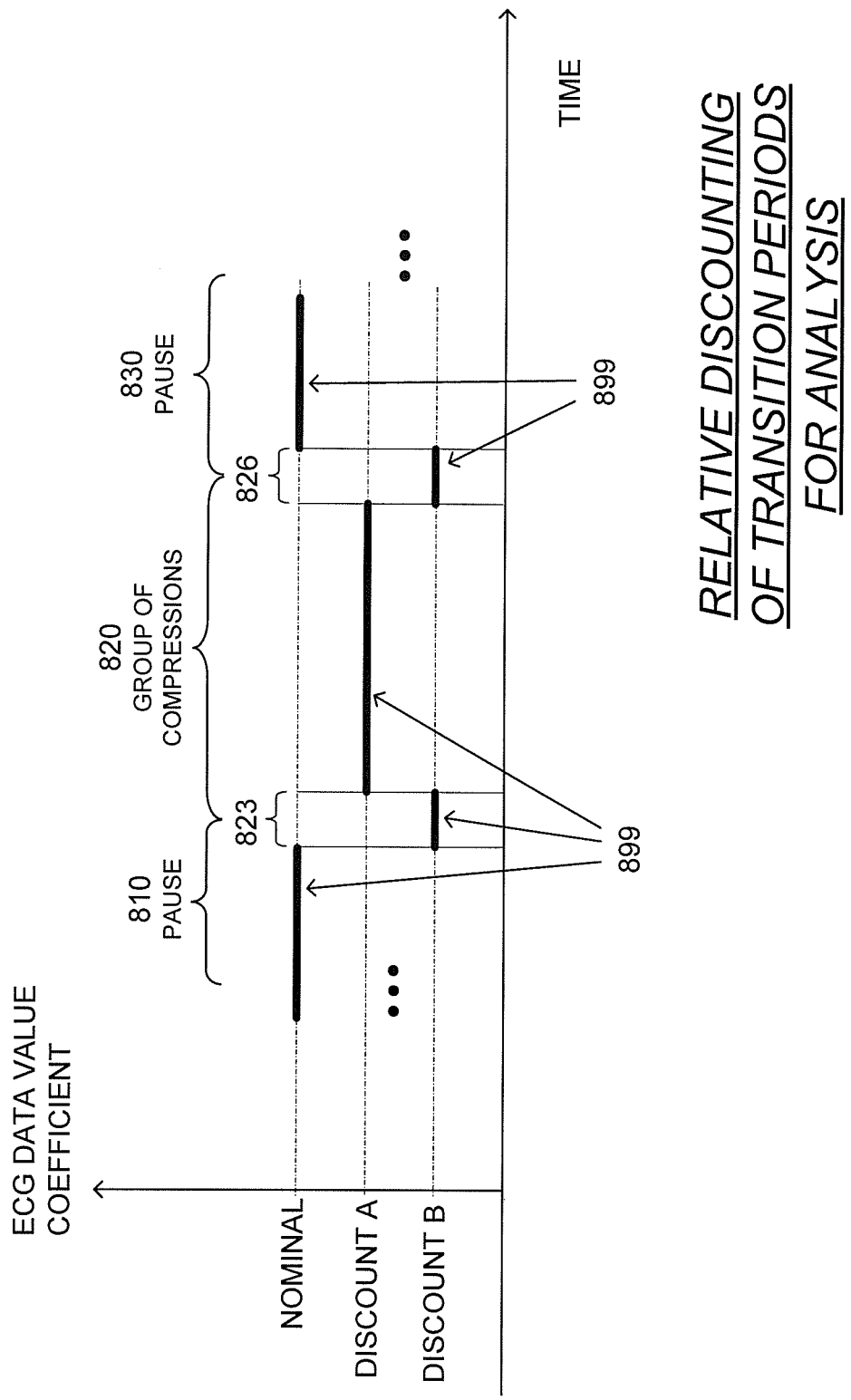
FIG. 8C is a diagram illustrating coefficient values applied to ECG data so as to effectuate differential discounting around CPR transition periods of patient ECG data according to embodiments.

In an operation 740 a first transition interval may be determined within the ECG data. For example, the processor may determine at least one of a beginning interval and an ending interval of the identified chest compression group. These intervals are also known as transition intervals. In certain embodiments, the transition interval has a duration of no more than two seconds. The processor may analyze a segment of the ECG data that includes both first ECG data occurring within the determined transition interval and second ECG data occurring outside the determined transition interval, the analysis discounting the first ECG data relative to the second ECG data, as shown at operation 750. Discounting is at least partial, but non-zero. In some embodiments, discounting is complete, meaning that the first ECG data is completely ignored. In these embodiments, the second ECG data may include data occurring both before and after the determined transition interval. FIG. 8C, discussed below, illustrates an example of the relative discounting of transition periods for analysis, such as that performed at operation 750.

In certain embodiments, the relative discounting performed at operation 750 may change responsive to an indication or determination that the patient has previously received at least one stored electrical charge. For example, the processor may reduce the value of a coefficient corresponding to the determined interval responsive to an indication or determination that the patient has previously received at least one stored electrical charge. Alternatively, the processor may at least substantially discard the first ECG data responsive to such an indication or determination.

In an optional operation 760, a second transition interval may be determined within the ECG data. In these embodiments, a segment of the ECG data may be analyzed that includes both the second ECG data occurring outside the first and second determined intervals and third ECG data occurring within the second determined interval, the analysis discounting the third ECG data relative to the second ECG data, as shown at operation 770. The second ECG data may include data occurring before the beginning interval, between the beginning and ending intervals, and after the ending interval. An example of the relative discounting performed at operation 770 is illustrated by FIG. 8C, which is discussed below.

As with the relative discounting performed at operation 750, the relative discounting performed at operation 770 may change responsive to an indication or determination that the patient has previously received at least one stored electrical charge. For example, the processor may reduce the value of a coefficient corresponding to the second determined interval responsive to an indication or determination that the patient has previously received at least one stored electrical charge or, alternatively, at least substantially discard the third ECG data responsive to such an indication or determination.

At operation 780, it may be determined whether a stored electrical charge should be guided to the patient based on the analysis. Responsive to a determination that the stored electrical charge should be guided to the patient, the processor may provide the rescuer with an indication that the stored electrical charge should be guided to the patient such as a visual or audio prompt; or cause that charge to be guided that way automatically, and so on.

FIG. 8A is a time diagram of patient ECG data periods where chest compression groups are alternated with pauses for ventilating the patient. A timeline 800 illustrates a first ECG data period 810 in which the rescuer temporarily pauses the delivery of chest compressions to perform ventilations on the patient. During a second ECG data period 820, the rescuer performs a group of chest compressions until a third ECG data period 830, during which the rescuer again pauses the delivery of chest compressions to perform ventilations on the patient.

During a fourth ECG data period 840, the rescuer performs a group of chest compressions until a fifth ECG data period 850, during which the rescuer again pauses the delivery of chest compressions to perform ventilations on the patient. During a sixth ECG data period 860, the rescuer performs a group of chest compressions until a seventh ECG data period 870, during which the rescuer again pauses the delivery of chest compressions to perform ventilations on the patient. In certain embodiments, the analysis performed by a processor may include identifying the occurrence of multiple chest compression groups within patient ECG data.

As the ECG data periods 810, 820, . . . , 870, . . . alternate, the transitions between them are not instantaneous, but actually occupy some time. This phenomenon is now described in more detail. In the example, a segment 821 begins during the first ECG data period 810 and ends during the third ECG data period 830, both of which are patient ventilation periods. The segment 821 includes a first transition interval, or beginning interval, that corresponds to transitioning between the first ECG data period 810 and the second ECG data period 820, as the rescuer stops ventilating the patient and resumes chest compressions. The segment 821 includes a second transition interval, or ending interval, that corresponds to transitioning between the second ECG data period 820 and the third ECG data period 830, when chest compressions are again stopped for patient ventilation. In certain embodiments, the segment 821 represents an identified chest compression group such as that discussed above in connection with FIG. 7. The transition intervals are described in more detail later in this document.

FIG. 8B is a time diagram of the segment 821 of the patient ECG data of FIG. 8A, showing the CPR transition periods around a single chest compression group according to embodiments. In the example, the segment 821 includes a first interval or beginning interval 823 that corresponds to the beginning 822 of the chest compressions delivered by the rescuer to the patient. The segment 821 also includes a second interval or ending interval 826 that corresponds to the ending 825 of the chest compressions delivered by the rescuer to the patient. For example, the rescuer may temporarily pause the delivery of the chest compressions to perform ventilations on the patient.

The beginning interval 823 may include one or more signal peaks 824 each having an amplitude that is significantly larger than that of each of the rest of the signal peaks within the beginning interval 823. The ending interval 826 may include one or more signal peaks 828 and 829 each having an amplitude that is significantly larger than that of each of the rest of the signal peaks within the ending interval 826.

FIG. 8C is a diagram illustrating coefficient values 899 applied to ECG data so as to effectuate differential discounting around CPR transition periods of patient ECG data according to embodiments. The diagram includes the first ECG data period 810, second ECG data period 820, and third ECG data period 830. The diagram also includes the first interval or beginning interval 823 and the second interval or ending interval 826.

The processor may apply coefficients 899 to chest compression group transition periods, such as the beginning interval 823 or ending interval 826 of the second ECG data period 820. These coefficients 899 may have or be assigned a first value corresponding to a first discount level, labeled "Discount B" in FIG. 8C. For example, the processor may discount first ECG data relative to second ECG data by applying a linear coefficient to the first ECG data, the linear coefficient corresponding to a first discount level. Referring to FIG. 8C, the processor may discount the ECG data corresponding to the beginning interval 823 to compensate for or otherwise address signal interference in the ECG data resulting from the beginning of the chest compressions delivered to the patient during the second ECG data period 820. The processor may also discount the ECG data corresponding to the ending interval 826 to compensate for or otherwise address signal interference in the ECG data resulting from the ending of the chest compressions delivered to the patient during the second ECG data period 820.

The processor may apply coefficients 899 to periods during which chest compressions are being delivered to the patient, such as 820. These coefficients 899 may have or be assigned a second value corresponding to a second discount level, labeled "Discount A" in FIG. 8C. For example, the processor may discount second ECG data by applying a second linear coefficient to data of second ECG data that occurs before a determined interval, the second linear coefficient corresponding to a second discount level. Referring to FIG. 8C, the processor may discount the ECG data corresponding to the second ECG data period 820 to compensate for or otherwise address signal interference in the ECG data resulting from the delivery of the chest compressions to the patient during the second ECG data period 820.

A processor may apply coefficients 899 to periods during which chest compressions are paused, such as 810 and 830. These coefficients 899 may have or be assigned a third value corresponding to a third discount level, labeled "Nominal" in FIG. 8C. For example, the processor may further discount second ECG data by applying a third linear coefficient to data of the second ECG data that occurs after the determined interval, the third linear coefficient corresponding to a third discount level. These coefficients 899 may have or be assigned a nominal value due to the absence of signal interference resulting from the delivery of chest compressions to the patient. In certain embodiments, no coefficients are applied to periods during which chest compressions are paused, such as 810 and 830.

Figure 9:
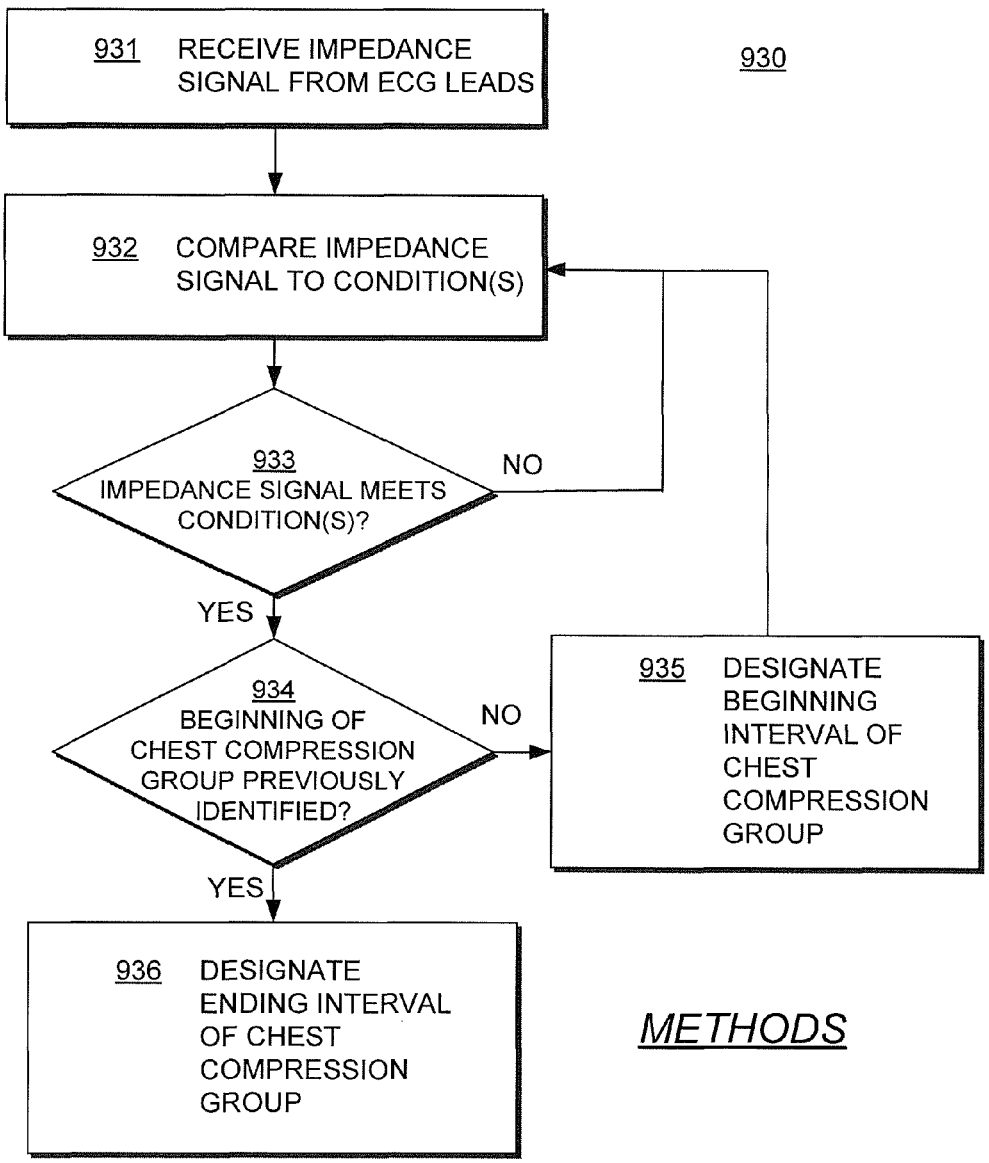
FIG. 9 is a flowchart for illustrating different a first sample embodiment of an operation of the flowchart of FIG. 7.
Figure 10:
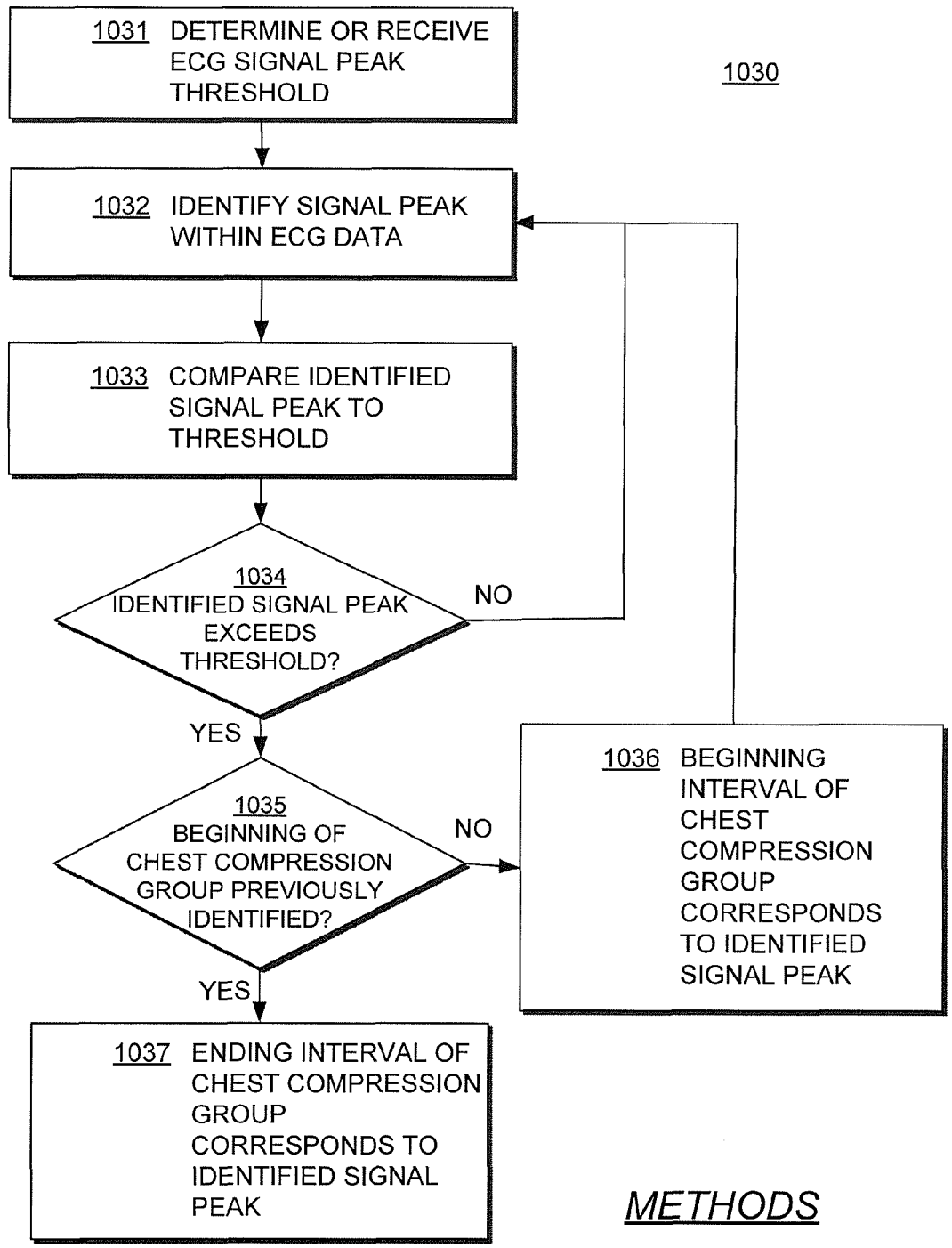
FIG. 10 is a flowchart for illustrating a second sample embodiment of an operation of the flowchart of FIG. 7.
Figure 11:
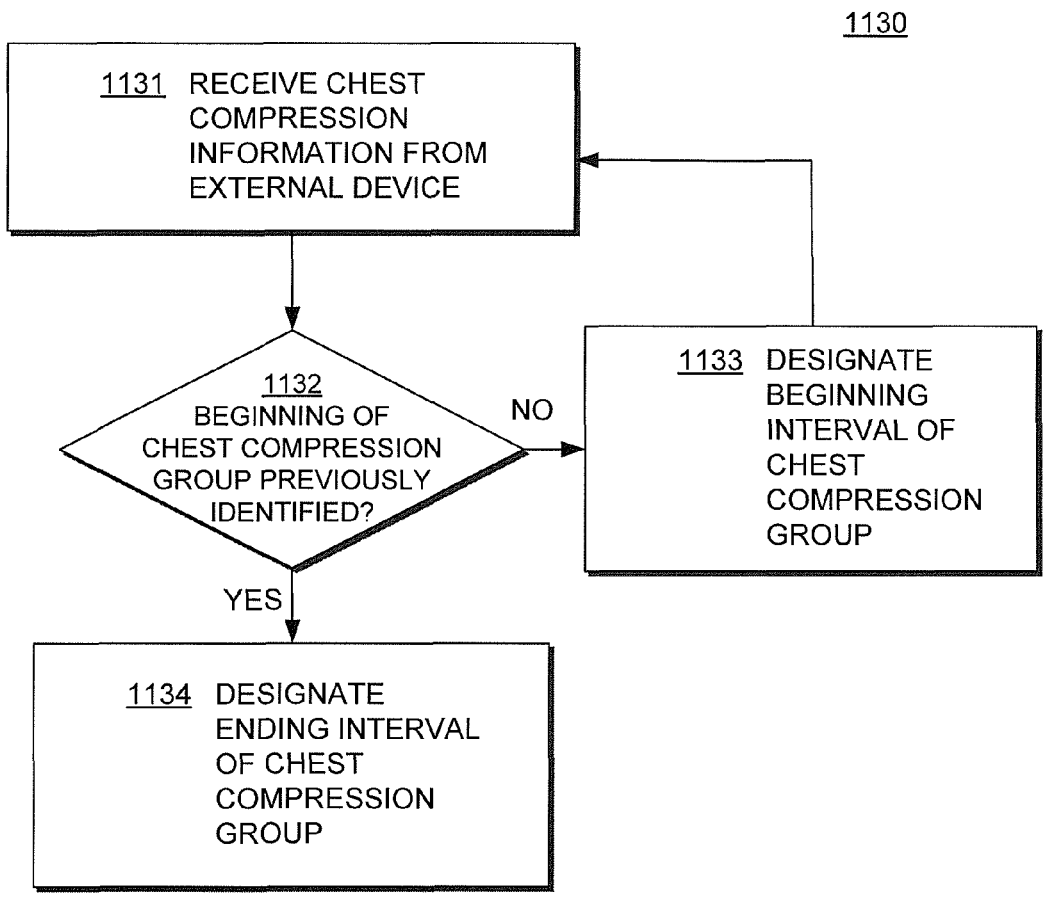
FIG. 11 is a flowchart for illustrating a second sample embodiment of an operation of the flowchart of FIG. 7.

FIGS. 9-11 are flowcharts for illustrating different sample embodiments of an operation of the flowchart of FIG. 7.

FIG. 9 illustrates a first embodiment 930 of the operation 730 of FIG. 7. A processor, such as the processor 330 illustrated in FIG. 3, may identify the occurrence of the at least one chest compression group by receiving an impedance signal from ECG leads on the patient, as shown at 931, and comparing the impedance signal to one or more conditions, as shown at 932. The conditions may include a predefined impedance threshold level, for example.

A determination may be made as to whether the impedance signal meets the one or more conditions, as shown at 933. Conditions could be any kind. Suitable conditions can be by determining "Root Mean Square" ("RMS") values. If the impedance signal does not meet the condition(s), processing may return to 932. If the impedance signal does meet the condition(s), however, a determination may be made as to whether the beginning of the identified chest compression group has been previously identified, as shown at 934.

If the beginning of the identified chest compression group has not been previously identified, the processor may store an indication that the beginning interval of the identified chest compression group corresponds to the identified signal peak, as shown at 935. If the beginning of the identified chest compression group has been previously identified, however, the processor may store an indication that the ending interval of the identified chest compression group corresponds to the identified signal peak, as shown at 936.

FIG. 10 illustrates a second embodiment 1030 of the operation 730 of FIG. 7. A processor, such as the processor 330 illustrated in FIG. 3, may identify the occurrence of the at least one chest compression group by determining or receiving an ECG signal peak threshold, as shown at 1031, detecting signal peaks of the ECG data, as shown at 1032, and comparing the detected signal peaks to the ECG signal peak threshold, as shown at 1033.

A determination may be made as to whether an identified signal peak exceeds the threshold, as shown at 1034. For example, in an embodiment where RMS values are considered, an ECG amplitude >4 mV P-P may occur mostly when compressions are present. A transition from >4 mV P-P to a typical ECG signal amplitude, i.e. one with <2 mV P-P, could indicate a CPR transition or a change greater than 2 times the baseline P-P voltage.

If the identified signal peak does not exceed the threshold, processing may return to 1032. If the identified signal peak does exceed the threshold, however, a determination may be made as to whether the beginning of the identified chest compression group has been previously identified, as shown at 1035.

If the beginning of the identified chest compression group has not been previously identified, the processor may store an indication that the beginning interval of the identified chest compression group corresponds to the identified ECG signal peak that exceeds the threshold, as shown at 1036. If the beginning of the identified chest compression group has been previously identified, however, the processor may store an indication that the ending interval of the identified chest compression group corresponds to the identified ECG signal peak that exceeds the threshold, as shown at 1037.

FIG. 11 illustrates a third embodiment 1130 of the operation 730 of FIG. 7. A processor, such as the processor 330 illustrated in FIG. 3, may identify the occurrence of the at least one chest compression group by analyzing chest compression information received from an external device, as shown at 1131. The chest compression information may indicate that a rescuer has initiated delivery of chest compressions to a patient, for example. Alternatively or in addition thereto, the chest compression information may indicate that a rescuer has completed delivery of chest compressions to a patient.

The external device may include a location sensor, an accelerometer, a force sensor, a capnography sensor, an optical sensor, a chest compression machine, a generator of CPR prompts, or a combination that includes one or more of these particular devices. In certain embodiments, the processor may identify the occurrence of the at least one chest compression group based on CPR prompt information originated for the use of a rescuer performing CPR on the patient, or by having communicated otherwise with such a sensor or machine.

If the beginning of the identified chest compression group has not been previously identified, the processor may store an indication that the beginning interval of the identified chest compression group corresponds to the identified signal peak, as shown at 1133. If the beginning of the identified chest compression group has been previously identified, however, the processor may store an indication that the ending interval of the identified chest compression group corresponds to the identified signal peak, as shown at 1134.

In this description, numerous details have been set forth in order to provide a thorough understanding. In other instances, well-known features have not been described in detail in order to not obscure unnecessarily the description.

A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems.

The following claims define certain combinations and sub-combinations of elements, features, steps, and/or functions, which are regarded as novel and non-obvious. Additional claims for other combinations and sub-combinations may be presented in this or a related document.

What is claimed is:

1. A medical device, comprising:
an energy storage module configured to store an electrical charge; and
a processor configured to:
receive ECG data of a patient receiving chest compressions;
identify the occurrence of a chest compression group within the received ECG data, the identified chest compression group corresponding to a series of consecutive, substantially periodically repeating chest compressions being administered to the patient;
determine, within the received ECG data, a first one of a beginning interval and an ending interval of the identified chest compression group, wherein the beginning interval corresponds to a first chest compression of the chest compression group and the ending interval corresponds to a final chest compression of the chest compression group;
analyze a segment of the ECG data that includes both first ECG data occurring within the first one of a beginning interval and an ending interval of the identified chest compression group and second ECG data occurring outside the first one of a beginning interval and an ending interval of the identified chest compression group, the analysis discounting partially but not completely the first ECG data relative to the second ECG data; and
determine whether stored electrical charge should be guided to the patient based on the analysis.

2. The medical device of claim 1, in which
the processor is configured to identify the occurrence of the chest compression group by:
determining or receiving an ECG signal peak threshold;
detecting signal peaks of the ECG data; and
comparing the detected signal peaks to the ECG signal peak threshold.

3. The medical device of claim 2, in which
the beginning interval of the chest compression group is determined by detecting an ECG signal peak that exceeds the threshold.

4. The medical device of claim 2, in which
the ending interval of the chest compression group is determined by detecting an ECG signal peak that exceeds the threshold.

5. The medical device of claim 1, in which
the processor is configured to identify the occurrence of the chest compression group by:
analyzing chest compression information received from an external device.

6. The medical device of claim 5, in which
the external device comprises at least one of: a location sensor, an accelerometer, a force sensor, a capnography sensor, or an optical sensor.

7. The medical device of claim 1, in which
the processor is configured to identify the occurrence of the chest compression group based on CPR prompt information originated for the use of a rescuer performing CPR on the patient.

8. The medical device of claim 1, in which
the determined first interval has a duration of no more than two seconds.

9. The medical device of claim 1, in which
the processor is further configured to:
change an amount of the discounting responsive to an indication or determination that the patient has previously received at least one stored electrical charge.

10. The medical device of claim 1, in which
the second ECG data includes data occurring both before and after the determined interval.

11. The medical device of claim 1, in which
the segment of the ECG data further includes third ECG data occurring within the second determined interval, the analysis discounting the third ECG data relative to the second ECG data.

12. The medical device of claim 11, in which
the second ECG data includes data occurring before the beginning interval, between the beginning and ending intervals, and after the ending interval.

13. The medical device of claim 1, in which
the processor is configured to discount the first ECG data relative to the second ECG data by applying a linear coefficient to the first ECG data, the linear coefficient corresponding to a first discount level.

14. The medical device of claim 13, in which
the processor is configured to discount the first ECG data relative to the second ECG data by applying a first linear coefficient to the first ECG data, the first linear coefficient corresponding to a first discount level, and in which the processor is further configured to discount the second ECG data by:
applying a second linear coefficient to data of the second ECG data that occurs before the determined interval, the second linear coefficient corresponding to a second discount level; and
applying a third linear coefficient to data of the second ECG data that occurs after the determined interval, the third linear coefficient corresponding to a third discount level.

15. The medical device of claim 1, in which
the processor is configured to identify the occurrence of the chest compression group by:
receiving an impedance signal from ECG leads on the patient; and
comparing the impedance signal to one or more impedance signal conditions.

16. A method, comprising:
receiving ECG data of a patient receiving chest compressions;
identifying the occurrence of a chest compression group within the received ECG data, the identified chest compression group corresponding to a series of consecutive, substantially periodically repeating chest compressions being administered to the patient;
determining, within the received ECG data, a first one of a beginning interval and an ending interval of the identified chest compression group, wherein the beginning interval corresponds to a first chest compression of the chest compression group and the ending interval corresponds to a final chest compression of the chest compression group;
analyzing a segment of the ECG data that includes both first ECG data occurring within the first one of a beginning interval and an ending interval of the identified chest compression group and second ECG data occurring outside the first one of a beginning interval and an ending interval of the identified chest compression group, the analysis discounting partially but not completely the first ECG data relative to the second ECG data; and
determining whether a stored electrical charge should be guided to the patient based on the analysis.

17. The method of claim 16, in which
identifying the occurrence of the chest compression group comprises:
determining or receiving an ECG signal peak threshold;
detecting signal peaks of the ECG data; and
comparing the detected signal peaks to the ECG signal peak threshold.

18. The method of claim 16, in which
identifying the occurrence of the chest compression group comprises:
analyzing chest compression information received from an external device.

19. The method of claim 16, in which
identifying the occurrence of the chest compression group comprises:
receiving an impedance signal from ECG leads on the patient;
comparing the impedance signal to one or more impedance signal conditions.

20. The method of claim 16, in which
the identifying is based on CPR prompt information originated for the use of a rescuer performing CPR on the patient.

21. The method of claim 16, in which
the determined first interval has a duration of no more than two seconds.

22. The method of claim 16, further comprising:
changing an amount of the discounting responsive to an indication or determination that the patient has previously received at least one stored electrical charge.

23. The method of claim 16, in which
discounting the first ECG data relative to the second ECG data comprises applying a linear coefficient to the first ECG data, the linear coefficient corresponding to a first discount level.

24. The method of claim 23, further comprising discounting the second ECG data by:
applying a second linear coefficient to data of the second ECG data that occurs before the determined interval, the second linear coefficient corresponding to a second discount level; and
applying a third linear coefficient to data of the second ECG data that occurs after the determined interval, the third linear coefficient corresponding to a third discount level.

* * * * *